United States Patent [19]

Diana et al.

[11] Patent Number: 5,175,177
[45] Date of Patent: Dec. 29, 1992

[54] 1,2,4-OXADIAZOLYL-PHENOXYALK-YLISOXAZOLES AND THEIR USE AS ANTIVIRAL AGENTS

[75] Inventors: Guy D. Diana, Stephentown; Thomas R. Bailey, Town of Bethlehem, both of N.Y.

[73] Assignee: Sterling Drug Inc., New York, N.Y.

[21] Appl. No.: 731,569

[22] Filed: Jul. 17, 1991

[51] Int. Cl.$^5$ .................. C07D 413/12; A61K 31/41
[52] U.S. Cl. ................................. 514/364; 548/131
[58] Field of Search .................. 514/364; 548/131

[56] References Cited

U.S. PATENT DOCUMENTS

| | | | |
|---|---|---|---|
| 4,843,087 | 6/1989 | Diana | 514/374 |
| 4,857,539 | 8/1989 | Diana et al. | 514/378 |
| 4,861,791 | 8/1989 | Diana et al. | 514/374 |
| 4,942,241 | 7/1990 | Diana et al. | 548/131 |
| 4,945,164 | 7/1990 | Diana | 548/247 |

OTHER PUBLICATIONS

Potts, Comprehensive Heterocyclic Chemistry, pp. 66-69 (1984).

*Primary Examiner*—Robert Gerstl
*Attorney, Agent, or Firm*—Frederik W. Stonner; Paul E. Dupont

[57] ABSTRACT

Compounds of the formula

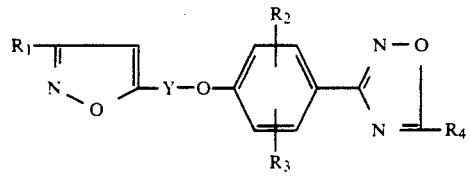

wherein:
Y is alkylene of 3 to 9 carbon atoms;
$R_1$ is lower-alkyl, lower-alkoxy-($C_{1-3}$-alkyl), lower-alkoxycarbonyl, cyclopropyl or trifluoromethyl;
$R_2$ and $R_3$ independently are hydrogen, lower-alkyl, halogen, lower-alkoxy, nitro, trifluoromethyl or hydroxy; and
$R_4$ is hydrogen or lower-alkyl; where lower-alkyl and lower-alkoxy, each occurrence, have from 1-5 carbon atoms;
with the proviso that when $R_1$ is lower-alkyl, at least one of $R_2$ and $R_3$ is hydroxy; or pharmaceutically acceptable acid-addition salts thereof are useful as antiviral agents, particularly against picornaviruses, including numerous strains of rhinovirus.

18 Claims, No Drawings

1,2,4-OXADIAZOLYL-PHENOXYALKYLISOX-AZOLES AND THEIR USE AS ANTIVIRAL AGENTS

BACKGROUND OF THE INVENTION a) Field of the Invention

This invention relates to novel 1,2,4-oxadiazolyl-phenoxyalkylisoxazoles, to methods for the preparation thereof, and compositions and methods for the use thereof as antiviral agents.

b) Information Disclosure Statement

Diana U.S. Pat. No. 4,843,087, issued Jun. 27, 1989, discloses heteryl-phenoxyalkylisoxazoles, wherein the heteryl moiety is an oxazole or an oxazine, which exhibit antiviral activity.

Diana et al. U.S. Pat. No. 4,857,539, issued Aug. 15, 1989, discloses antivirally active compounds of the formula

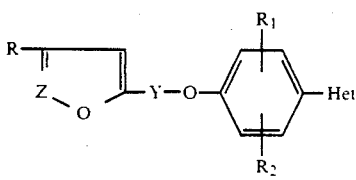

wherein:
Y is an alkylene bridge of 3-9 carbon atoms;
Z is N or HC;
R is hydrogen or lower-alkyl of 1-5 carbon atoms, with the proviso that when Z is N, R is lower-alkyl;
$R_1$ and $R_2$ are hydrogen, halogen, lower-alkyl, lower-alkoxy, nitro, lower-alkoxycarbonyl or trifluoromethyl; and
Het is selected from specified heterocyclic groups. Included in the definition of Het is unsubstituted 1,3,4-oxadiazol-2-yl and unsubstituted 1,2,4-oxadiazol-5-yl.

Diana et al. U.S. Pat. No. 4,861,791, issued Aug. 29, 1989, discloses antivirally active compounds of the formula, inter alia,

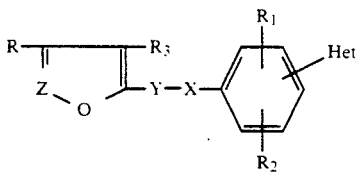

wherein:
Y is an alkylene bridge of 3 to 9 carbon atoms optionally interrupted by one or two oxygen atoms, by cyclohexyl or by an olefinic linkage;
X is O, S, SO or $SO_2$;
Z is N or $R_8C$, where $R_8$ is hydrogen or lower-alkanoyl;
$R_1$ and $R_2$ are selected from the group consisting of hydrogen, lower-alkyl, lower-alkenyl, halogen, nitro, lower-alkoxy, lower-alkylthio, difluoromethyl, trifluoromethyl, amino, lower-alkanoylamino, di-lower-alkylamino, hydroxy, lower-alkenoyl, lower-alkanoyl, hydroxymethyl and carboxy;
R and $R_3$ are each hydrogen or alkyl of 1 to 3 carbon atoms optionally substituted by a member of the group consisting of hydroxy, lower-alkanoyloxy, lower-alkoxy, halo or N=Z′, wherein N=Z′ is amino, lower-alkanoylamino, lower-alkylamino, di-lower-alkylamino, 1-pyrrolidyl, 1-piperidinyl or 4-morpholinyl; with the proviso that when Z is N, R is other than hydrogen; and
Het is selected from specified heterocyclic groups including unsubstituted 1,3,4-oxadiazol-2-yl.

Diana et al. U.S. Pat. No. 4,942,241, issued Jul. 17, 1990, discloses antivirally active compounds of the formulas

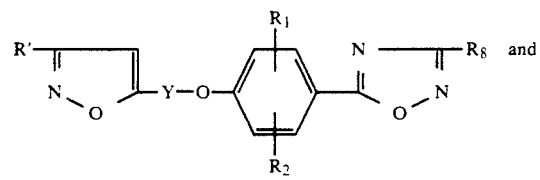

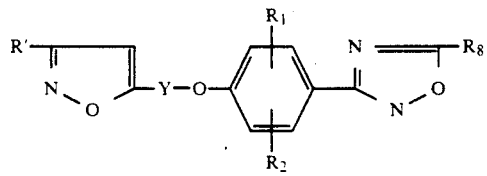

wherein:
Y is an alkylene bridge of 1-9 carbon atoms;
R′ is lower-alkyl or hydroxy-lower-alkyl of 1-5 carbon atoms;
$R_1$ and $R_2$ are hydrogen, halogen, lower-alkyl, lower-alkoxy, nitro, lower-alkoxycarbonyl or trifluoromethyl; and
$R_8$ is hydrogen or lower-alkyl of 1-5 carbon atoms.

Diana U.S. Pat. No. 4,945,164, issued Jul. 31, 1990, discloses antivirally active compounds of the formula, inter alia,

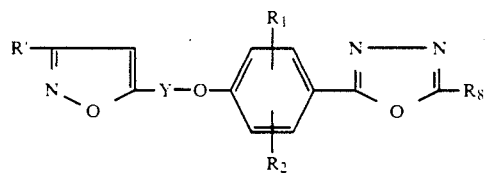

wherein:
Y is an alkylene bridge of 3-9 carbon atoms;
R′ is lower-alkyl or hydroxy-lower-alkyl of 1-5 carbon atoms;
$R_1$ and $R_2$ are hydrogen, halogen, lower-alkyl, lower-alkoxy, nitro, lower-alkoxycarbonyl or trifluoromethyl; and
$R_8$ is hydrogen or lower-alkyl of 1-5 carbon atoms.

SUMMARY OF THE INVENTION

The present invention relates to compounds of the formula

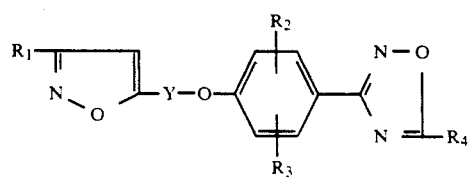

wherein:
Y is alkylene of 3 to 9 carbon atoms;

$R_1$ is lower-alkyl, lower-alkoxy-($C_{1-3}$-alkyl), lower-alkoxycarbonyl, cyclopropyl or trifluoromethyl;

$R_2$ and $R_3$ independently are hydrogen, lower-alkyl, halogen, lower-alkoxy, nitro, trifluoromethyl or hydroxy; and $R_4$ is hydrogen or lower-alkyl; where lower-alkyl and lower-alkoxy, each occurrence, have from 1-5 carbon atoms;

with the proviso that when $R_1$ is lower-alkyl, at least one of $R_2$ and $R_3$ is hydroxy; or pharmaceutically acceptable acid-addition salts thereof.

A preferred class of compounds within the scope of Formula I is that of the formula

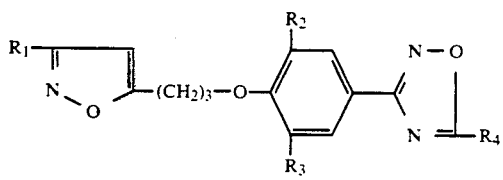

II

A particularly preferred class is that of Formula II wherein $R_1$ is lower-alkoxy-($C_{1-3}$-alkyl).

The invention also relates to compositions for combatting viruses comprising an antivirally effective amount of a compound of Formula I in admixture with a suitable carrier or diluent, and to methods of combatting viruses therewith, including the systemic treatment of viral infections in a mammalian host.

DETAILED DESCRIPTION INCLUSIVE OF PREFERRED EMBODIMENTS

The compounds of Formula I are sufficiently basic to form stable acid-addition salts with strong acids, and said salts are within the purview of the invention. The nature of the acid-addition salt is immaterial, provided it is derived from an acid the anion of which is essentially non-toxic to animal organisms. Examples of appropriate acid-addition salts include the hydrochloride, hydrobromide, sulfate, acid sulfate, maleate, citrate, tartrate, methanesulfonate, p-toluenesulfonate, dodecyl sulfate, cyclohexanesulfamate, and the like.

When the term halogen is used to define the substituents $R_1$ and $R_2$, any of the four common halogens, fluorine, chlorine, bromine or iodine are contemplated.

The terms lower-alkyl and lower-alkoxy refer to such groups having from one to five carbon atoms.

The compounds of Formula I can be prepared by a process which comprises reacting a compound of the formula

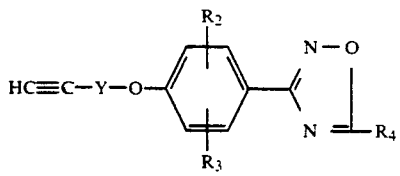

III with a nitrile oxide of the formula $R_1CN \rightarrow O$ (IVA) which is prepared in situ from a hydroxyimidoyl halide of the formula $R_1C(X)=NOH$ (IV), where X is chlorine or bromine, which may be prepared in situ, in the presence of an amine base, e.g., triethylamine, pyridine or N-methylpyrrolidine. The hydroxyimino halides of Formula IV belong to a generically known class of compounds and are readily prepared by conventional procedures, e.g., by reacting the corresponding aldehyde oxime ($R_1C=NOH$) with a halogenating agent, e.g., N-chlorosuccinimide or bromine. The process for preparing the compounds of Formula I by reacting the intermediates of Formulas III and IVA takes place by heating the reactants in an inert polar solvent, e.g., dimethylformamide or N-methylpyrrolidone, at a temperature in the range of about 20° to about 120° C.

The intermediates of Formula III are conveniently prepared according to the following flow sheet where X is chlorine or bromine and $X_1$ is chlorine, bromine or iodine:

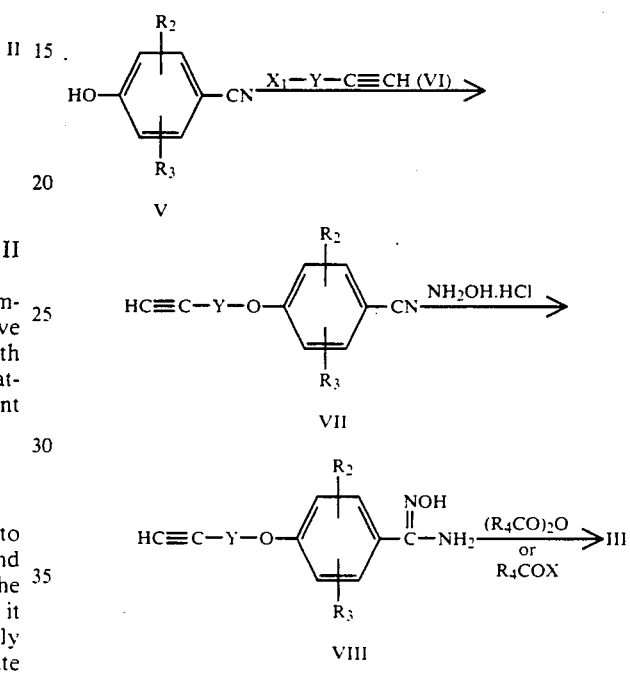

The cyanophenol V reacts with the haloalkyne VI in the presence of a base, e.g. potassium carbonate or sodium hydroxide, optionally with a catalytic amount of potassium iodide, in an inert polar solvent, e.g., N-methylpyrrolidone, at a temperature in the range of about 50° to about 120° C. to form the cyano compound VII. The cyano compound VII reacts with hydroxylamine hydrochloride in the presence of a base, e.g., sodium acetate, sodium carbonate or sodium hydroxide, in an alcoholic solvent, e.g., ethyl alcohol, at a temperature in the range of about 50° to about 150° C. to form the hydroximinoamide VIII. The hydroximinoamide VIII reacts with the acid anhydride $(R_4CO)_2O$, which serves as solvent, at a temperature in the range of about 50° to about 150° C. to form the intermediate of formula III. Alternatively the hydroximinoamide VIII reacts with the acid halide $R_4COX$ either in the presence of a base, e.g., sodium acetate, sodium carbonate or sodium hydroxide and in an inert solvent, e.g., methylene chloride, chloroform, toluene or tetrahydrofuran; or in a basic solvent, e.g., pyridine, at a temperature in the range of about 80° to about 130° C. to form the intermediate of formula III. The reaction of the acid anhydride or acid halide will, in the case where $R_2$ and/or $R_3$ are hydroxy, cause ester formation with the hydroxy, which esters can be hydrolyzed to the free hydroxy compound using conventional procedure such as aqueous alkaline hydrolysis.

The compounds of Formula III can also be prepared by the procedures described in U.S. Pat. No. 4,942,241.

The compounds of Formula I wherein $R_1$ is other than lower-alkoxycarbonyl can also be prepared by a process comprising cyclization of a compound of the formula

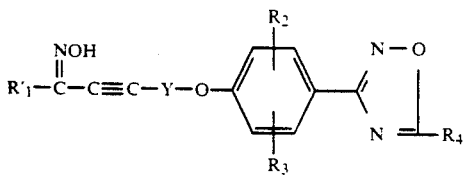

where $R'_1$ is lower-alkyl, lower-alkoxy-$(C_{1-3}$-alkyl), cyclopropyl or trifluoromethyl. The cyclization is carried out by heating compound X in an inert solvent, e.g., benzene, toluene or xylene, at a temperature in the range of about 50° to about 100° C.

The intermediate compounds of Formula X are conveniently prepared according to the following flow sheet.

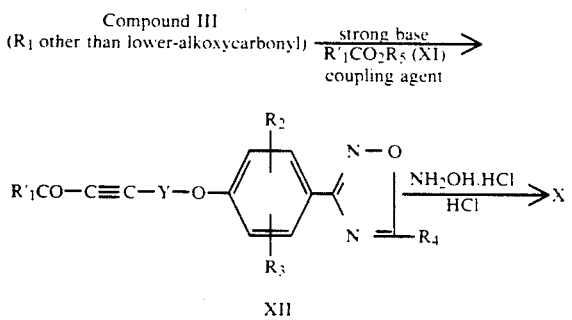

The compound of Formula III is reacted with approximately an equimolar amount of the compound of Formula XI (where $R_5$ can be, e.g., lower-alkyl, phenyl or benzyl) in an anhydrous inert solvent, e.g., tetrahydrofuran, in the presence of a coupling agent, e.g., boron trifluoride etherate, and a strong base, e.g., butyl lithium, lithium hydride, sodium hydride or an alkali metal salt of N-methylacetamide, at a temperature in the range of about −50° to about −80° C. to form the compound of Formula XII. Compound XII reacts with hydroxylamine hydrochloride in the presence of a catalytic amount of hydrogen chloride in an organic acidic solvent, e.g., acetic acid or propionic acid, at a temperature in the range of about 10° to about 40° C. to form the intermediate of Formula X.

The compounds of Formula I where $R_1$ is lower-alkyl and $R_2$ and/or $R_3$ is hydroxy can also be prepared by a process comprising reacting an oxadiazole of the formula

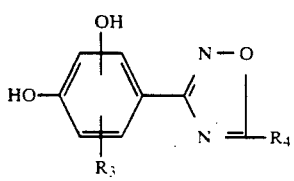

with an isoxazole of the formula

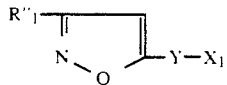

where $R''_1$ is lower-alkyl and $X_1$ is chlorine, bromine or iodine.

The oxadiazole XIII reacts with the isoxazole XIV in an inert polar solvent, e.g., acetonitrile or N-methylpyrrolidine, in the presence of a base, e.g., potassium carbonate or sodium hydroxide, optionally in the presence of a catalytic amount of sodium iodide, at a temperature in the range of about 50° to about 150° C.

The reaction of oxadiazole XIII with isoxazole XIV can, by virtue of the presence of at least two hydroxyl groups on the phenyl ring, forms a mixture of positional isomers which are readily separable using conventional procedures.

The intermediate oxadiazole of Formula XIII is conveniently prepared by reacting a cyano compound of the formula

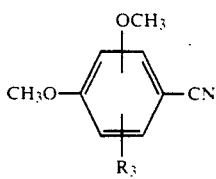

with hydroxylamine hydrochloride to form the hydroximinoamide of the formula

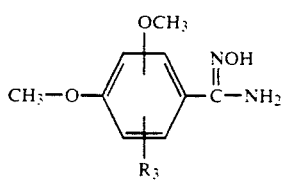

which in turn is reacted with an acid anhydride of formula $(R_4CO)_2O$ or acid halide of formula $R_4COX$ to form the oxadiazole of the formula

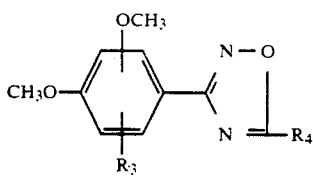

The procedures employed are described hereinabove for the preparation of the compound of Formula VIII and its conversion to the compound of Formula III. Oxadiazole XVII in turn is subjected to ether cleavage using conventional procedures, e.g., reaction with boron tribromide in an inert solvent such as methylene chloride at elevated temperatuers to form the intermediate of Formula XIII.

The intermediate cyano compounds of Formula XV belong to a generically well known class of compounds and can be readily prepared by conventional procedures. For example they can be prepared by treating the corresponding benzaldehyde oxime with a dehydrating agent such as 1,1'-carbonyldiimidazole. The benzaldehyde oxime in turn is readily prepared by reacting the corresponding aldehyde with hydroxylamine hydrochloride. These procedures are illustrated in Example 8 hereinbelow.

The intermediate isoxazoles of Formula XIV and their preparation are described in U.S. Pat. No. 4,942,241.

The structures of the compounds of the invention were established by modes of synthesis and elementary analysis, and by infrared, nuclear magnetic resonance and/or mass spectra.

The following examples will further illustrate the invention.

EXAMPLE 1 a) 3,5-Dimethyl-4-(3-ethinylpropoxy)benzonitrile

A mixture of 40 g 3,5-dimethyl-4-hydroxybenzonitrile, 32 ml 5-chloro-1-pentyne (d=0.968) and 74.63 g milled potassium carbonate in 25 ml N-methylpyrrolidine was heated under nitrogen at 100° C. with stirring for four hours. The mixture, after cooling to room temperature and addition of 300 ml water, was extracted with ethyl acetate. The ethyl acetate extracts were washed with aqueous 2N sodium hydroxide solution and saturated sodium chloride solution, dried ($MgSO_4$) and then concentrated in vacuo. The residue was subjected to flash filtration (activated magnesium silicate; ether/hexane) and the filtrate was concentrated in vacuo to give, after recrystallization (methyl alcohol/0° C.) 34.64 g of the title compound.

b) 3-[3,5-Dimethyl-4-(3-ethinylpropoxy)phenyl]-5-methyl-1,2,4-oxadiazole

A mixture of 25 g of the product from part (a), 16.6 g hydroxylamine hydrochloride and 32.64 g sodium acetate trihydrate in 200 ml ethyl alcohol and 40 ml water was heated at reflux for five hours. The mixture was cooled to room temperature and concentrated in vacuo. A suspension of the residue in 200 ml acetic anhydride was heated at reflux for two hours, cooled to room temperature and was treated at ice bath temperature and with stirring with aqueous 2N sodium hydroxide solution until basic (exothermic reaction/gas evolution). The reaction mixture was extracted with ether and the ether extracts were washed with aqueous sodium hydroxide (gas evolution) and dilute aqueous sodium bicarbonate solution until gas evolution ceased. The ether extracts were dried ($MgSO_4$) and concentrated in vacuo. The resulting residue was subjected to filtration (activated magnesium silicate; 15:85 ethyl acetate/hexane) and chromatography (MPLC, activated magnesium silicate; 15:85 ethyl acetate/hexane) to give 17.82 g of the title compound.

c) 5-{3-[2,6-Dimethyl-4-(5-methyl-1,2,4-oxadiazol-3-yl)phenoxy]propyl}-3-ethoxycarbonylisoxazole (I; $R_1=CO_2CH_2CH_3$; $R_2$ and $R_3=2,6-(CH_3)_2$, $R_4=CH_3$, $Y=(CH_2)_3$)

To a solution of 10.0 g ethyl chloro(hydroxyimino)acetate in N-methylpyrrolidone in a nitrogen atmosphere was added dropwise, with stirring, 6 g of the product from part (b) and stirring was continued for about 15 minutes at room temperature. The reaction mixture then was heated to 80°-90° C. and 9.3 ml of triethylamine was added slowly over a period of 5 hours. The reaction mixture was heated at 80°-90° C. for a further hour, poured into cold water and extracted with methylene chloride. The methylene chloride extracts were washed several times with water and finally with saturated sodium chloride solution, dried ($MgSO_4$) and concentrated in vacuo. The residue was subjected to flash filtration (activated magnesium silicate; 30:70 ethyl acetate/hexane) and chromatography (MPLC activated magnesium acetate; 30:70 ethyl acetate/hexane) to yield, after recrystallization from methyl alcohol, 5.97 g of the title compound, m.p. 95°-96° C.

EXAMPLE 2 a) Methoxyacetaldehyde Oxime

A mixture of 20.23 g methoxyacetaldehyde and 31.59 g hydroxylamine hydrochloride in 70 ml water was stirred at 45° C. for one-half hour. The solution was salted with sodium chloride and extracted with methylene chloride. The methylene chloride extracts were dried ($MgSO_4$) and concentrated in vacuo to yield 5.24 g of the title compound.

b) 5-{3-[2,6-Dimethyl-4-(5-methyl-1,2,4-oxadiazol-3-yl)phenoxy]propyl}-3-methoxymethylisloxazole (I; $R_1=CH_3OCH_2$, $R_2$ and $R_3=2,6-(CH_3)_2$, $R_4=CH_3$, $Y=(CH_2)_3$)

To a stirred solution of 1.97 g N-chlorosuccinimide in 20 ml dry dimethylformamide in a nitrogen atmosphere there was added two drops of pyridine and, after fifteen minutes, a solution of 1.32 g methoxyacetaldehyde oxime from part (a) above in 5 mls dry dimethylformamide dropwise during twenty minutes. Stirring was continued one hour and 2.0 g 3-[3,5-dimethyl-4-(3-ethinylpropoxy)phenyl]-5-methyl-1,2,4-oxadiazole, prepared by a procedure similar to that described in Example 1(b), then was added in one portion, the mixture was heated to 92° C. and 1.50 g of triethylamine in 10 mls dimethylformamide was added during twenty minutes. The reaction mixture was heated for one hour, cooled, poured into water and extracted with ethyl acetate. The ethyl acetate extracts were washed with 10% aqueous potassium bisulfate solution, water and saturated sodium chloride solution, dried ($MgSO_4$), filtered through activated magnesium silicate and concentrated in vacuo. The residue was subjected to successive ($2\times$) chromatography (MPLC, silica gel; 20:80 ($1\times$) and 15:85 ($1\times$) ethyl acetate/hexane) to yield 1.59 g of the title compound as a clear, colorless oil.

EXAMPLE 3 a) Ethoxyacetaldehyde Oxime

The title compound (10.11 g) was obtained as a pale yellow oil by reacting 16.20 g ethoxyacetaldehyde diethylacetal and 18.76 g hydroxylamine hydrochloride in 40 mls water and 25 mls ethyl alcohol following a procedure similar to that of Example 2(a).

b) 5-{3-[2,6-Dimethyl-4-(5-methyl-1,2,4-oxadiazol-3-yl)phenoxy]propyl}-3-ethoxymethylisoxazole (I; $R_1=CH_3CH_2OCH_2$, $R_2$ and $R_3=2,6-(CH_3)_2$, $R_4=CH_3$, $Y=(CH_2)_3$.

Following a procedure similar to that described in Example 2(b) and using 1.97 g N-chlorosuccinimide in 20 ml dimethylformamide, two drops of pyridine, 1.53 g ethoxyacetaldehyde oxime from part (a) above in 15 mls dimethylformamide, 2 g 3-[3,5-dimethyl-4-(3-ethinyl-propoxy)phenyl]-5-methyl-1,2,4-oxadiazole, prepared by a procedure similar to that described in Example 1(b) and 1.5 g triethylamine in 20 ml dimethylformamide, there was obtained after chromatography (MPLC, silica gel; 20:80 ethyl acetate/hexane) and recrystallization (methyl alcohol/−78° C.), 1.06 g of the title compound, m.p. 45.5°–46° C.

EXAMPLE 4 a) Cyclopropanecarboxaldehyde Oxime

To a solution of 18.76 g hydroxylamine hydrochloride in 40 mls water was added 27 mls 10% aqueous sodium hydroxide solution and 7.0 g cyclopropanecarboxaldehyde and the solution was heated at 40°–50° C. for one-half hour. Water (30 mls) was added and the mixture was extracted with ethyl ether. The ethyl ether extracts were washed with saturated sodium chloride solution, dried (MgSO$_4$) and concentrated in vacuo to yield 3.88 g of the title compound as white crystals.

b) 3-Cyclopropyl-5-{3-[2,6-dimethyl-4-(5-methyl-1,2,4-oxadiazol-3-yl)phenoxy]propyl}isoxazole (I; $R_1$=cyclopropyl, $R_2$ and $R_3$=2,6-(CH$_3$)$_2$, $R_4$=CH$_3$, Y=(CH$_2$)$_3$)

Following a procedure similar to that described in Example 2(b) and using 0.52 g N-chlorosuccinimide in 5 mls dimethylformamide, two drops of pyridine, 0.33 g cyclopropanecarboxaldehyde oxime from part (a) above in 10 mls dimethylformamide, 0.53 g 3-[3,5-dimethyl-4-(3-ethinylpropoxy)phenyl]-5-methyl-1,2,4-oxadiazole prepared by a procedure similar to that described in Example 1(b), and 0.40 g triethylamine in 20 mls dimethylformamide, there was obtained after chroamtography (MPLC, silica gel; 20:80 ethyl acetate/hexane) and recrystallization (methyl alcohol) 0.312 g of the title compound, m.p. 50.5°–51° C.

EXAMPLE 5 a) 3-[3,5-Dimethyl-4-(3-ethinylpropoxy)phenyl]-5-ethyl-1,2,4-oxadiazole.

A stirred mixture of 4.33 g 3,5-dimethyl-4-(3-ethinylpropoxy)benzonitrile, prepared by a procedure similar to that described in Example 1(a), 7.05 hydroxylamine hydrochloride and 17.54 g milled potassium carbonate in 75 mls ethyl alcohol was heated overnight at reflux in a nitrogen atmosphere. The mixture was filtered to remove salts which were washed with ethyl alcohol. The filtrate was concentrated in vacuo to provide 5.71 g of a residue of yellow oil and solid. A solution of this residue in 10 mls pyridine and under a nitrogen atmosphere was treated dropwise with stirring with 4.26 g of propionyl chloride at a rate which maintained reflux (exothermic reaction). Stirring was continued one-half hour after addition was completed and the reaction mixture was cooled and extracted with ethyl acetate. The ethyl acetate extracts were washed with water, 1N hydrochloric acid, water and saturated sodium chloride solution, dried (MgSO$_4$) and concentrated in vacuo. The residual orange oil was subjected to chromatography (MPLC, silica gel; 20:80 ethyl acetate/hexane) to yield 4.70 g of the title compound as a clear, colorless oil.

b) 5-{3-[2,6-Dimethyl-4-(5-ethyl-1,2,4-oxadiazol-3-yl)phenoxy]propyl}-3-methoxymethylisoxazole (I; $R_1$=CH$_3$OCH$_2$, $R_2$ and $R_3$=2,6-di(CH$_3$)$_2$, $R_4$=CH$_2$CH$_3$, Y=(CH$_2$)$_3$.

Following a procedure similar to that described in Example 2(b) and using 3.75 g N-chlorosuccinimide in 15 mls dimethylformamide, three drops of pyridine, 2.5 g methoxyacetaldehyde oxime in 10 mls dimethylformamide, 4 g of 3-[3,5-dimethyl-4-(3-ethinylpropoxy)-phenyl]-5-ethyl-1,2,4-oxadiazole from part (a) above in 5 mls dimethylformamide and 2.85 g triethylamine in 20 mls dimethylformamide, there was obtained after successive (3×) chromatography (MPLC, silica gel; 20:80 (1×) and 15:85 (2×) ethyl acetate/hexane) 2.565 g of the title compound as a clear, colorless oil.

EXAMPLE 6 a) 3,5-Dichloro-4-(3-ethinylpropoxy)benzonitrile

A mixture of 10.0 g 3,5-dichloro-4-hydroxybenzonitrile, 6.2 mls 5-chloro-1-pentyne, 18.38 g milled potassium carbonate (100%) and 0.88 g potassium iodide in 125 mls N-methylpyrrolidone was heated at 60° C. with stirring overnight. An additional 4.6 g milled potassium carbonate and 2.82 mls 5-chloro-1-pentyne was added and heating was continued for two days. The reaction mixture was poured into water and extracted with ethyl acetate. The ethyl acetate extracts were washed with aqueous 10% potassium bisulfate solution, water and saturated sodium chloride solution, dried (MgSO$_4$) and concentrated in vacuo. The resulting oily residue was subjected to flash chromatography (silica gel; 10:90 ethyl acetate/hexane) to yield 7.03 g of the title compound.

b) 3-[3,5-Dichloro-4-(3-ethinylpropoxy)phenyl]-5-methyl-1,2,4-oxadiazole

A stirred mixture of 6.0 g 3,5-dichloro-4-(3-ethinylpropoxy)benzonitrile from part (a) above, 8.20 g hydroxylamine hydrochloride and 20.39 g milled potassium carbonate in 100 mls absolute ethyl alcohol was heated at reflux overnight. The mixture was filtered to remove salts which were washed with ethyl alcohol and the filtrate was concentrated in vacuo to provide 8.32 g of a white solid. A stirred suspension of this solid in 20 mls pyridine was treated dropwise with 3.70 g acetyl chloride at a rate which maintained gentle reflux (exothermic reaction). Heating at reflux was continued for three hours. The reaction mixture was diluted with water and chilled. The aqueous layer was decanted from the slightly gummy solid which was then washed with water and dissolved in methylene chloride. The methylene chloride solution was dried (MgSO$_4$) and subjected to flash chromatography (MPLC, silica gel; methylene dichloride) and chromatography (MPLC, silica gel; 20:80 ethyl acetate/hexane) to yield 3.43 g of the title compound.

c) 5-{3-[2,6-Dichloro-4-(5-methyl-1,2,4-oxadiazol-3-yl)phenoxy]propyl}-3-methoxymethylisoxazole (I; $R_1$=CH$_3$OCH$_2$, $R_2$ and $R_3$=2,6-(Cl)$_2$, $R_4$=CH$_3$, Y=(CH$_2$)$_3$)

Following a procedure similar to that described in Example 2(b) and using 1.61 g N-chlorosuccinimide in 15 mls dimethylformamide, three drops of pyridine, 1.07 g methoxyacetaldehyde oxime in 15 mls dimethylformamide, 1.80 g of 3-[3,5-dichloro-4-(3-ethinylpropoxy)phenyl]-5-methyl-1,2,4-oxadiazole from part (b) above and 1.22 g triethylamine in 20 mls dimethylformamide, there was obtained after flash chromatography (silica gel; 50:50 ethyl acetate/hexane) and chromatography (MPLC, silica gel; 20:80 ethyl acetate/hexane) and recrystallization (methyl alcohol) 0.546 g of the title compound as a white solid, m.p. 55.5°–56° C.

EXAMPLE 7 a)

3-{3,5-Dimethyl-4-[3-(trifluoroacetylethinyl)propoxy]phenyl}-5-methyl-1,2,4-oxadiazole A solution of 2.0 g 3-[3,5-dimethyl-4-(3-ethinylpropoxy)phenyl]-5-methyl-1,2,4-oxadiazole, prepared by a procedure similar to that described in Example 1(b), in 50 mls anhydrous tetrahydrofuran in an argon atmosphere was chilled to about $-70°$ C. To this solution there was added 3.7 mls butyl lithium followed by ethyl trifluoroacetate and, after ten minutes, 1.5 mls boron trifluoride ethereate. The solution was stirred for five hours at $-70°$ C. and then overnight without cooling, quenched with 20 mls aqueous ammonium chloride solution, diluted with water and extracted with ethyl ether. The ethyl ether extracts were dried ($Na_2SO_4$) and concentrated in vacuo. The residue was subjected to column chromatography (silica gel; 20:80 to 40:60 ethyl ether/hexane) to give 497 mg of the title compound as an oil.

b)

5-{3-[2,6-Dimethyl-4-(5-methyl-1,2,4-oxadiazol-3-yl)phenoxy]propyl}-3-trifluoromethylisoxazole (I: $R_1 = CF_3$, $R_2$ and $R_3 = 2,6\text{-}(CH_3)_2$, $R_4 = CH_3$, $Y = (CH_2)_3$)

To 479 mg of 3-{3,5-dimethyl-4-[3-(trifluoroacetylethinyl)propoxy]phenyl}-5-methyl-1,2,4-oxadiazole from part (a) above and 509 mg hydroxylamine hydrochloride in 10 mls of acetic acid at ambient room temperature was added with stirring 1 ml 1M hydrochloric acid. After twenty hours an additional 1 ml 1M aqueous hydrochloric acid and 1.00 g hydroxylamine hydrochloride were added and stirring was continued for five days. The reaction mixture was poured into 200 mls water and extracted with ethyl ether. The ethyl ether extracts were washed with water, dried ($Na_2SO_4$) and concentrated. A solution of the residue (470 mg) in benzene was heated at reflux overnight, cooled, diluted with methylene chloride, washed with aqueous 1.5M potassium bicarbonate and water, filtered through silica gel and concentrated. The oily residue was subjected to preparative TLC (silica gel; methylene dichloride) to yield 92 mg of the title compound, m.p. 62°–64.5° C.

By carrying out the procedure described in Example 2(b) but replacing the 3-[3,5-dimethyl-4-(3-ethinylpropoxy)phenyl]-5-methyl-1,2,4-oxadiazole with an equimolar amount of 3-[4-(3-ethinylpropoxy)phenyl]-5-methyl-1,2,4-oxadiazole, 3-[4-(3-ethinylpropoxy)-3-nitrophenyl]-5-methyl-1,2,4-oxadiazole, 3-[4-(3-ethinylpropoxy)-2-methoxyphenyl]-5-methyl-1,2,4-oxadiazole, 3-[4-(3-ethinylpropoxy)-3-trifluoromethylphenyl]-5-methyl-1,2,4-oxadiazole or 3-[4-(3-ethinylpropoxy)-3-methoxycarbonylphenyl-5-methyl-1,2,4-oxadiazole, there can be obtained, respectively, 5-{3-[4-(5-methyl-1,2,4-oxadiazol-3-yl)phenoxy]propyl}-3-methoxymethylisoxazole (I; $R_1 = CH_3OCH_2$, $R_2$ and $R_3$ each is H, $R_4 = CH_3$, $Y = (CH_2)_3$), 5-{3-[4-(5-methyl-1,2,4-oxadiazol-3-yl)-2-nitrophenoxy]propyl}-3-methoxymethylisoxazole (I; $R_1 = CH_3OCH_2$, $R_2 = 2\text{-}NO_2$, $R_3 = H$, $R_4 = CH_3$, $Y = (CH_2)_3$), 5-{3-[3-methoxy-4-(5-methyl-1,2,4-oxadiazol-3-yl)phenoxy]propyl}-3-methoxymethylisoxazole (I; $R_1 = CH_3OCH_2$, $R_2 = 3\text{-}OCH_3$, $R_3 = H$, $R_4 = CH_3$, $Y = (CH_2)_3$), 5-{3-[4-(5-methyl-1,2,4-oxadiazol-3-yl)-2-trifluoromethylphenoxy]propyl}-3-methoxymethylisoxazole (I; $R_1 = CH_3OCH_2$, $R_2 = 2\text{-}CF_3$, $R_3 = H$, $R_4 = CH_3$, $Y = (CH_2)_3$) or 5-{3-[2-methoxycarbonyl-4-(5-methyl-1,2,4-oxadiazol-3-yl)-phenoxy]propyl}-3-methoxymethylisoxazole (I; $R_1 = CH_3OCH_2$, $R_2 = 2\text{-}CO_2CH_3$, $R_3 = H$, $R_4 = CH_3$, $Y = (CH_2)_3$).

The above intermediate (ethinylpropoxy)phenyloxadiazoles in turn can be obtained by carrying out the procedure described in Example 1(b) but replacing the 3,5-dimethyl-4-(3-ethinylpropoxy)benzonitrile with an equimolar amount of, respectively, 4-(3-ethinylpropoxy)benzonitrile, 4-(3-ethinylpropoxy)-3-nitrobenzonitrile, 4-(3-ethinylpropoxy)-2-methoxybenzonitrile, 4-(3-ethinylpropoxy)-3-trifluoromethylbenzonitrile or 4-(3-ethinylpropoxy)-3-methoxycarbonylbenzonitrile.

The above intermediate (ethinylpropoxy)benzonitriles in turn can be obtained by carrying out the procedure described in Example 1(a) but replacing the 3,5-dimethyl-4-hydroxybenzonitrile with an equimolar amount of, respectively, 4-hydroxybenzonitrile, 4-hydroxy-3-nitrobenzonitrile, 4-hydroxy-2-methoxybenzonitrile, 4-hydroxy-3-trifluoromethylbenzonitrile or 4-hydroxy-3-methoxycarbonylbenzonitrile.

By carrying out the procedure described in Example 2(b) but replacing the 3-[3,5-dimethyl-4-(3-ethinylpropoxy)phenyl]-5-methyl-1,2,4-oxadiazole with an equimolar amount of 3-[3,5-dimethyl-4-(5-ethinylpentoxy)phenyl]-5-methyl-1,2,4-oxadiazole or 3-[3,5-dimethyl-4-(9-ethinylnonyloxy)phenyl]-5-methyl-1,2,4-oxadiazole, there can be obtained, respectively, 5-{5-[2,6-dimethyl-4-(5-methyl-1,2,4-oxadiazol-3-yl)phenoxy]pentyl}-3-methoxymethylisoxazole (I; $R_1 = CH_3OCH_2$, $R_2$ and $R_3 = 2,6\text{-}(CH_3)_2$, $R_4 = CH_3$, $Y = (CH_2)_5$) or 5-{9-[2,6-dimethyl-4-(5-methyl-1,2,4-oxadiazol-3-yl)phenoxy]nonyl}-3-methoxymethylisoxazole (I; $R_1 = CH_3OCH_2$, $R_2$ and $R_3 = 2,6\text{-}(CH_3)_2$, $R_4 = CH_3$, $Y = (CH_2)_9$).

The above intermediate (ethinylpentoxy)phenyloxadiazole and (ethinylnonyloxy)phenyloxadiazole in turn can be obtained by carrying out the procedure described in Example 1(b) but replacing the 3,5-dimethyl-4-(3-ethinylpropoxy)benzonitrile with an equimolar amount, respectively, of 3,5-dimethyl-4-(5-ethinylpentoxy)benzonitrile or 3,5-dimethyl-4-(9-ethinylnonyloxy)benzonitrile.

The above intermediate (ethinylpentoxy)benzonitrile and (ethinylnonyloxy)benzonitrile in turn can be obtained by following the procedure described in Example 1(a) but replacing the 5-chloro-1-pentyne with an equimolar amount of, respectively, 7-chloro-1-heptyne or 11-chloro-1-undecyne.

EXAMPLE 8 a) 2,4-Dimethoxy-3-methylbenzaldehyde Oxime

A mixture of 25.1 g 2,4-dimethoxybenzaldehyde, 19.46 g hydroxylamine hydrochloride and 22 mls pyridine in 150 mls ethyl alcohol was heated at reflux with stirring for two hours, allowed to cool, and concentrated in vacuo. The residue was treated with water and stirring and the resulting white solid was collected by filtration to give 26.8 g of the title compound. m.p. 110°–111° C.

b) 2,4-Dimethoxy-3-methylbenzonitrile

A mixture of 21.69 g of the product from part (a) above and 21.08 g 1,1'-carbonyldiimidazole in 100 mls methylene chloride was heated at reflux in a nitrogen atmosphere with stirring for two hours, allowed to cool, washed with 3N hydrochloric acid solution, water and saturated sodium chloride solution, dried ($MgSO_4$) and concentrated in vacuo to give 19.61 g of the title compound as a yellow oil which formed crystals on cooling.

c) 3-(2,4-Dimethoxy-3-methylphenyl)-5-methyl-1,2,4-oxadiazole

A mixture of 1.77 g of the product from part (b) above, 2.08 g hydroxylamine hydrochloride and 4.08 g sodium acetate trihydrate in 25 mls ethyl alcohol and 5 mls water was heated at reflux with stirring for one day, allowed to cool and concentrated in vacuo. The residue in 25 mls acetic anhydride was heated at reflux for six hours, allowed to cool and poured into 200 mls 10% aqueous sodium hydroxide and made strongly basic with 35% aqueous sodium hydroxide. The resulting tan gum was collected by filtration and recrystallized (methyl alcohol) to give 0.83 g of the title compound, m.p. 105°–107° C.

d) 3-(2,4-Dihydroxy-3-methylphenyl)-5-methyl-1,2,4-oxadiazole

To a stirred solution of 0.70 g of the product from part (c) above in 10 mls methylene chloride was added 15 mls of 1M boron tribromide in methylene chloride (exothermic to reflux). The stirred solution was heated at reflux for two hours, allowed to cool, poured into ice cold water with stirring and extracted with methylene chloride. The methylene chloride extracts were washed with saturated sodium chloride solution, dried ($MgSO_4$/charcoal) and concentrated in vacuo. The residue in 2N sodium hydroxide was heated on a steam bath, treated with charcoal, filtered, chilled on ice, acidified with concentrated hydrochloric acid and filtered to give an off-white solid. From a solution of this solid in methyl alcohol only a small amount (0.057 g) of the title product, m.p. 230°–231° C., was isolated. The solution was concentrated to yield 0.225 g of the title compound, m.p. 224°–225° C.

By following a procedure similar to that described in Example 1(a) but substituting for the 3,5-dimethyl-4-hydroxybenzonitrile an equimolar amount of the compound from Example 8, part (d), there can be obtained 3-[4-(3-ethinylpropoxy)-2-hydroxy-3-methylphenyl]-5-methyl-1,2,4-oxadiazole and its positional isomer 3-[2-(3-ethinylpropoxy)-4-hydroxy-3-methylphenyl]-5-methyl-1,2,4-oxadiazole which can be separated by conventional procedures.

By following the procedure described in Example 2(b) but replacing the methoxyacetaldehyde oxime with an equimolar amount of butyraldehyde oxime or acetaldehyde oxime and the 3-[3,5-dimethyl-4-(3-ethinylpropoxy)phenyl]-5-methyl-1,2,4-oxadiazole with an equimolar amount of 3-[4-(3-ethinylpropoxy)-2-hydroxy-3-methylphenyl]-5-methyl-1,2,4-oxadiazole, there can be obtained, respectively, 5-{3-[3-hydroxy-2-methyl-4-(5-methyl-1,2,4-oxadiazol-3-yl)phenoxy]propyl}-3-(n-propyl)isoxazole (I; $R_1=CH_3CH_2CH_2$, $R_2=$3-OH, $R_3=$2-$CH_3$, $R_4=CH_3$, $Y=(CH_2)_3$ or 5-{3-[3-hydroxy-2-methyl-4-(5-methyl-1,2,4-oxadiazol-3-yl)phenoxy]propyl}-3-methylisoxazole (I; $R_1=CH_3$, $R_2=$3-OH, $R_3=$2-$CH_3$, $R_4=CH_3$, $Y=(CH_2)_3$).

By following a procedure similar to that described in Example 1(a) but replacing the 3,5-dimethyl-4-hydroxybenzonitrile with an equimolar amount of 3-(2,4-dihydroxy-3-methylphenyl)-5-methyl-1,2,4-oxadiazole from part (d) of Example 8 and the 5-chloro-1-pentyne with an equimolar amount of 5-(3-chloropropyl)-3-(n-propyl)isoxazole or 5-(3-chloropropyl)-3-methylisoxazole, there can be obtained, respectively, a mixture of the positional isomers 5-{3-[3-hydroxy-2-methyl-4-(5-methyl-1,2,4-oxadiazol-3-yl)phenoxy]propyl}-3-(n-propyl)isoxazole (I; $R_1=CH_3CH_2CH_2$, $R_2=$3-OH, $R_3=$2-$CH_3$, $R_4=CH_3$, $Y=(CH_2)_3$ and 5-{3-{3-hydroxy-2-methyl-6-(5-methyl-1,2,4-oxadiazol-3-yl)phenoxy]propyl}-3-(n-propyl)isoxazole or 5-{3-[3-hydroxy-2-methyl-4-(5-methyl-1,2,4-oxadiazol-3-yl)phenoxy]propyl{-3-methylisoxazole (I; $R_1=CH_3$, $R_2=$3-OH, $R_3=$2-$CH_3$, $R_4=CH_3$, $Y=(CH_2)_3$) and 5-{3-[3-hydroxy-2-methyl-6-(5-methyl-1,2,4-oxadiazol-3-yl)phenoxy]propyl}-3-methylisoxazole, which isomers can be separated using conventional procedures.

Biological evaluation of compounds of Formulas I and II has shown that they possess antiviral activity. They are useful in inhibiting virus replication in vitro and are primarily active against picornaviruses, including enteroviruses, polioviruses, echovirus and coxsackie virus, and especially numerous strains of rhinoviruses. The in vitro testing of the compounds of the invention against picornaviruses showed that viral replication was inhibited at minimum inhibitory concentrations (MIC) ranging from about 0.003 to about 3 micrograms per milliliter. One of two test procedures was used as follows:

PROCEDURE 1

The MIC values were determined by a standard plaque reduction assay as follows: HeLa (Wisconsin) cells in monolayers were infected at a concentration of virus to give approximately 80 plaques per monolayer in the virus control (no drug present). The compound to be tested was serially diluted and included in the agar-medium overlay and in some cases, during the adsorption period as well. The MIC was determined to be the concentration of compound which reduced the number of plaques by 50% with respect to the untreated virus control.

PROCEDURE 2

The MIC values were determined by an automated tissue culture infectious dose 50% (TCID-50) assay. HeLa (Wisconsin) cells in 96-well cluster plates were infected with a dilution of virus which had been shown empirically to produce 80% to 100% cytopathic effect (CPE) in 3 days in the absence of drug. The compound to be tested was serially diluted through 10, 2-fold cycles and added to the infected cells. After a 3 day incubation at 33° C. and 2.5% carbon dioxide, the cells were fixed with a 5% solution of glutaraldehyde followed by staining with a 0.25% solution of crystal violet in water. The plates were then rinsed, dried, and the amount of stain remaining in the well (a measure of intact cells) was quantitated with an optical density reader. The MIC was determined to be the concentration of compound which protected 50% of the cells from virus-induced CPE relative to an untreated virus control.

In the above test procedures, the compounds were tested against a panel of fifteen human rhinovirus (HRV) serotypes, namely HRV-2, -1A, -1B, -6, -14, -21, -22, -15, -25, -30, -50, -67, -89, -86 and -41 and the MIC value, expressed in micrograms per milliliter (μg/ml), for each rhinovirus serotype was determined.

The following Table gives the testing results with the compounds of the invention. The compound of Example 1(c) was tested in accordance with Procedure 1 above; the compounds of Examples 2b–5b, 6(c) and 7(b) were tested in accordance with Procedure 2 above.

| HRV Serotype | IN VITRO ACTIVITY (μg/ml) Example: | | | | | |
|---|---|---|---|---|---|---|
|  | 1(c) | 2(b) | 3(b) | 4(b) | 5(b) | 6(c) | 7(b) |
| −2 | NT | 0.0030 | 0.0050 | 0.0090 | 0.0060 | 0.010 | 0.040 |
| −1A | I | 0.023 | 0.042 | 0.034 | 0.077 | 0.034 | 0.060 |
| −1B | NT | 0.0090 | 0.015 | NT | 0.069 | 0.018 | NT |
| −6 | NT | 0.136 | 0.045 | 0.84 | 0.039 | 0.073 | NT |
| −14 | NT | 0.044 | NT | 0.039 | 0.045 | 0.036 | 0.305 |
| −21 | NT | 0.0040 | 0.0080 | 0.0090 | 0.010 | 0.0090 | NT |
| −22 | NT | 0.0080 | 0.018 | 0.011 | 0.0080 | 0.0090 | 0.032 |
| −15 | NT | 0.148 | 0.312 | NT | 0.189 | 0.137 | 0.232 |
| −25 | NT | 0.019 | 0.014 | 0.0060 | 0.0030 | 0.022 | NT |
| −30 | NT | 0.015 | 0.047 | 0.048 | 0.033 | 0.015 | 0.065 |
| −50 | NT | 0.032 | 0.070 | 0.042 | 0.027 | 0.074 | 0.190 |
| −67 | NT | 0.047 | 0.106 | 0.080 | 0.126 | 0.067 | 0.161 |
| −89 | 2.6 | 0.0030 | 0.0030 | 0.0070 | 0.0040 | 0.0050 | 0.019 |
| −86 | NT | 0.078 | 0.045 | NT | 0.025 | 0.072 | NT |
| −41 | NT | 0.145 | 0.153 | 0.142 | 0.173 | 0.154 | 0.536 |

(NT = not tested;
I = inactive)

The antiviral compositions are formulated for use by preparing a dilute solution or suspension in a pharmaceutically acceptable aqueous, organic or aqueous-organic medium for topical or parenteral administration by intravenous or intramuscular injection, or for intranasal or ophthalmic application; or are prepared in tablet, capsule, or aqueous suspension form with conventional excipients for oral administration.

We claim:

1. A compound of the formula

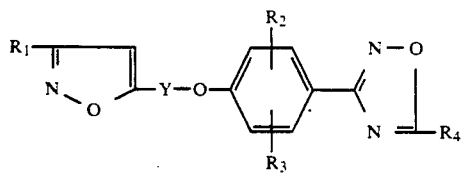

wherein:
Y is alkylene of 3 to 9 carbon atoms;
$R_1$ is lower-alkyl, lower-alkoxy-($C_{1-3}$-alkyl), lower-alkoxycarbonyl, cyclopropyl or trifluoromethyl;
$R_2$ and $R_3$ independently are hydrogen, lower-alkyl, halogen, lower-alkoxy, nitro, trifluoromethyl or hydroxy; and
$R_4$ is hydrogen or lower-alkyl; where lower-alkyl and lower-alkoxy, each occurence, have from 1–5 carbon atoms;
with the proviso that when $R_1$ is lower-alkyl, at least one of $R_2$ and $R_3$ is hydroxy; or pharmaceutically acceptable acid-addition salts thereof.

2. A compound according to claim 1 of the formula

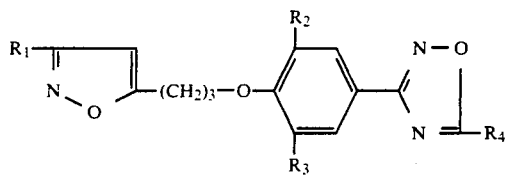

3. A compound according to claim 2 wherein $R_2$ and $R_3$ independently are lower-alkyl or halogen.

4. 5-{3-[2,6-Dimethyl-4-(5-methyl-1,2,4-oxadiazol-3-yl)phenoxy]propyl}-3-ethoxycarbonylisoxazole according to claim 2.

5. 3-Cyclopropyl-5-{3-[2,6-dimethyl-4-(5-methyl-1,2,4-oxadiazol-3-yl)phenoxy]propyl}isoxazole according to claim 2.

6. 5-{3-[2,6-Dimethyl-4-(5-methyl-1,2,4-oxadiazol-3-yl)phenoxy]propyl}-3-trifluoromethylisoxazole according to claim 2.

7. A compound according to claim 1 wherein $R_1$ is lower-alkoxy-($C_{1-3}$-alkyl).

8. A compound according to claim 2 wherein $R_1$ is lower-alkoxy-($C_{1-3}$-alkyl).

9. A compound according to claim 8 wherein $R_2$ and $R_3$ independently are lower-alkyl or halogen.

10. 5-{3-[2,6-Dimethyl-4-(5-methyl-1,2,4-oxadiazol-3-yl)phenoxy]propyl}-3-methoxymethylisoxazole according to claim 9.

11. 5-{3-[2,6-Dimethyl-4-(5-methyl-1,2,4-oxadiazol-3-yl)phenoxy]propyl}-3-ethoxymethylisoxazole according to claim 9.

12. 5-{3-[2,6-Dimethyl-4-(5-ethyl-1,2,4-oxadiazol-3-yl)phenoxy]propyl}-3-methoxymethylisoxazole according to claim 9.

13. 5-{3-[2,6-Dichloro-4-(5-methyl-1,2,4-oxadiazol-3-yl)phenoxy]propyl}-3-methoxymethylisoxazole according to claim 9.

14. A composition for combatting picornaviruses which comprises an antivirally effective amount of a compound according to claim 1, in admixture with a suitable carrier or diluent.

15. A composition according to claim 14 for combatting rhinoviruses.

16. A method for combatting picornaviruses which comprises contacting the locus of said viruses with a compound according to claim 1.

17. A method for combatting a picornaviral infection in a mammalian host which comprises administering to said host an antivirally effective amount of a composition according to claim 14.

18. A method for combatting a rhinovirus infection in a mammalian host which comprises administering to said host an antivirally effective amount of a composition according to claim 15.

* * * * *